United States Patent

Wollweber et al.

Patent Number: 4,973,350
Date of Patent: Nov. 27, 1990

[54] FUNGICIDAL 1-AMINOMETHYL-3-(2-FLUORO-3-CHLOROPHENYL)-4-CYANOPYRROLE DERIVATIVES

[75] Inventors: Detlef Wollweber, Wuppertal; Wilhelm Brandes, Leichlingen, both of Fed. Rep. of Germany

[73] Assignee: Bayer Aktiengesellschaft, Leverkusen, Fed. Rep. of Germany

[21] Appl. No.: 307,390

[22] Filed: Feb. 6, 1989

[30] Foreign Application Priority Data

Feb. 11, 1988 [DE] Fed. Rep. of Germany ....... 3804128

[51] Int. Cl.$^5$ ................. C07D 405/12; C07D 409/12; A01N 43/36
[52] U.S. Cl. ........................................ 71/3; 548/517; 548/527
[58] Field of Search ....................... 548/517, 527; 71/3

[56] References Cited

FOREIGN PATENT DOCUMENTS 0130149 1/1985 European Pat. Off. .
0133247 2/1985 European Pat. Off. .
3702852 8/1988 Fed. Rep. of Germany .
3702853 8/1988 Fed. Rep. of Germany .

OTHER PUBLICATIONS

Chemical Abstracts, vol. 95, No. 21, Nov. 23, 1981.

Primary Examiner—Robert A. Wax
Assistant Examiner—Frederick F. Tsung
Attorney, Agent, or Firm—Sprung Horn Kramer & Woods

[57] ABSTRACT

Fungicidal 1-aminomethyl-3-(2-fluoro-3-chlorophenyl)-4-cyano-pyrrole derivatives of the formula

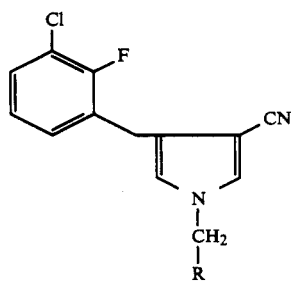

(I)

in which
R stands for a

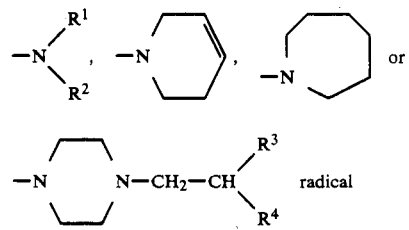

radical where
R$^1$ stands for optionally substituted alkyl, for alkenyl, alkinyl or cycloalkyl, or for in each case optionally substituted aralkyl or aryl,
R$^2$ stands for in each case optionally substituted heterocyclylalkyl, heterocyclylalkenyl, heterocyclylalkinyl or heterocyclyl, for dialkylaminoalkyl or for in each case optionally substituted cycloalkylalkyl or phenethyl,
R$^3$ stands for hydrogen or alkyl and
R$^4$ stands for cyano, alkanoyl, alkoxycarbonyl, alkylaminocarbonyl, dialkylaminocarbonyl, for alkylsulphinyl, for alkylsulphonyl, for phenylsulphinyl or for phenylsulphonyl.

The compound where R is replaced by an election-withdrawing leaving group is a novel intermediate.

9 Claims, No Drawings

FUNGICIDAL 1-AMINOMETHYL-3-(2-FLUORO-3-CHLOROPHENYL)-4-CYANOPYRROLE DERIVATIVES

This invention relates to new 1-aminomethyl-3-(2-fluoro-3-chlorophenyl)-4-cyano-pyrrole derivatives, several processes for their preparation and their use as pesticides, in particular as fungicides.

It is known that certain 3-aryl-pyrroles, such as, for example, 4-cyano-3-(2,3-dichlorophenyl)-pyrrole possess good fungicidal properties (cf., for example, EP No. 174,910 or EP No. 182,738 or EP No. 133,247).

Furthermore, 3-aryl-4-cyano-pyrroles are known which are substituted in the 1-position and which have not previously been published; these possess fungicidal properties (cf. unpublished German Patent Applications Nos. 3,702,852 and 3,702,853).

New 1-aminomethyl-3-(2-fluoro-3-chlorophenyl)-4-cyano-pyrrole derivatives of the general formula (I)

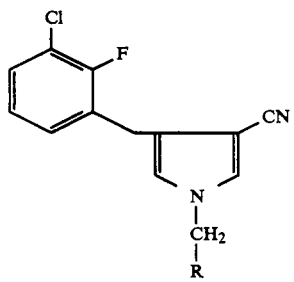
(I)

in which
R stands for a

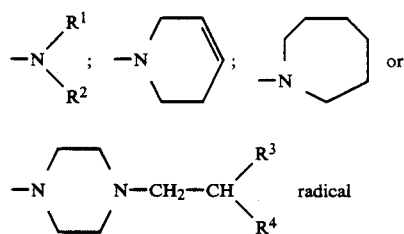

where
R$^1$ stands for optionally substituted alkyl, for alkenyl, alkinyl or cycloalkyl, or for in each case optionally substituted aralkyl or aryl,
R$^2$ stands for in each case optionally substituted heterocyclylalkyl, heterocyclylalkenyl, heterocyclylalkinyl or heterocyclyl, for dialkylaminoalkyl or for in each case optionally substituted cycloalkylalkyl or phenethyl,
R$^3$ stands for hydrogen or alkyl and
R$^4$ stands for cyano, alkanoyl, alkoxycarbonyl, alkylaminocarbonyl, dialkylaminocarbonyl, for alkylsulphinyl, for alkylsulphonyl, for phenylsulphinyl or for phenylsulphonyl,
have been found.

Furthermore, it has been found that the new 1-aminomethyl-3-(2-fluoro-3-chlorophenyl)-4-cyano-pyrrole derivatives of the general formula (I)

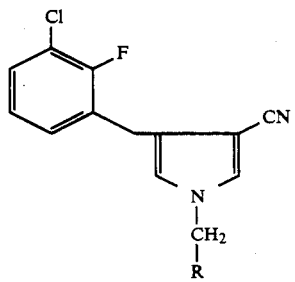
(I)

in which
R stands for a

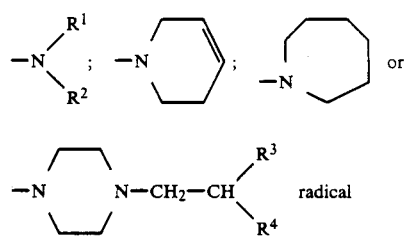

where
R$^1$ stands for optionally substituted alkyl, for alkenyl, alkinyl or cycloalkyl, or for in each case optionally substituted aralkyl or aryl,
R$^2$ stands for in each case optionally substituted heterocyclylalkyl, heterocyclylalkenyl, heterocyclylalkinyl or heterocyclyl, for dialkylaminoalkyl or for in each case optionally substituted cycloalkylalkyl or phenethyl,
R$^3$ stands for hydrogen or alkyl and
R$^4$ stands for cyano, alkanoyl, alkoxycarbonyl, alkylaminocarbonyl, dialkylaminocarbonyl, for alkylsulphinyl, for alkylsulphonyl, for phenylsulphinyl or for phenylsulphonyl,
are obtained when (a) 3-(2-fluoro-3-chlorophenyl)-4-cyano-pyrrole of the formula (II)

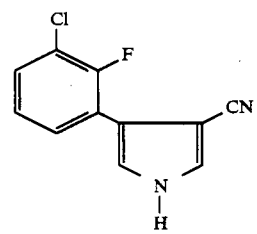
(II)

is reacted with formaldehyde and amines of the formula (III)

R—H (III)

in which
R has the abovementioned meaning, if appropriate in the presence of a diluent and if appropriate in the presence of a reaction auxiliary, or when (b) 3-(2-fluoro-3-chlorophenyl)-4-cyano-pyrroles of the formula (IV)

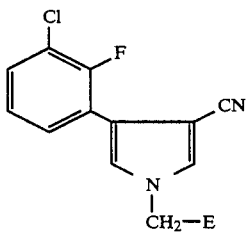 (IV)

in which

E stands for an electron-withdrawing leaving group, are reacted with amines of the formula (III)

H—R (III)

in which

R has the abovementioned meaning,
if appropriate in the presence of a diluent and if appropriate in the presence of an acid-binding agent.

Finally, it has been found that the new 1-amino-methyl-3-(2-fluoro-3-chlorophenyl)-4-cyano-pyrrole derivatives of the general formula (I) possess a good action against pests, above all against fungi.

Formula (I) provides a general definition of the 1-aminomethyl-3-(2-fluoro-3-chlorophenyl)-4-cyano-pyrrole derivatives according to the invention. Preferred compounds of the formula (I) are those in which R stands for a

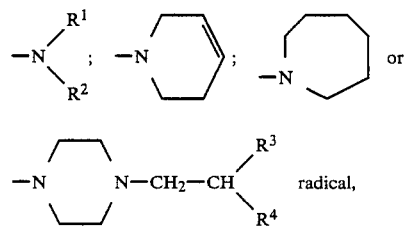

where $R^1$ stands for an optionally substituted straightchain or branched alkyl having 1 to 6 carbon atoms, suitable substituents being: cyano, cycloalkyl having 3 to 7 carbon atoms, in each case straight-chain or branched alkoxy, alkylcarbonyl, alkoxycarbonyl, alkylaminocarbonyl, dialkylaminocarbonyl, alkylsulphinyl, alkylsulphonyl or dialkylamino, each having 1 to 6 carbon atoms in the individual alkyl moieties; furthermore for in each case straight-chain or branched alkenyl or alkinyl, each having 3 to 6 carbon atoms, for cycloalkyl having 3 to 7 carbon atoms, or for phenyl or benzyl which are in each case optionally monosubstituted to polysubstituted in the phenyl moiety by identical or different substituents, suitable substituents in each case being: halogen, cyano, in each case straight-chain or branched alkyl, alkoxy, halogenoalkyl, halogenoalkoxy, alkylcarbonyl or alkoxycarbonyl, each having 1 to 6 carbon atoms in the individual alkyl moieties and in the case of the halogenoalkyl or halogenoalkoxy radical each having 1 to 9 identical or different halogen atoms, $R^2$ stands for in each case straight-chain or branched heterocyclylalkyl having 1 to 6 carbon atoms in the alkyl moiety, heterocyclylalkenyl having 3 to 6 carbon atoms in the alkenyl moiety, heterocyclylalkinyl having 3 to 6 carbon atoms in the alkinyl moiety or heterocyclyl, heterocyclyl in each case standing for a 5- to 7- membered unsaturated or saturated heterocyclic ring having 1 to 3 hetero atoms, in particular nitrogen, oxygen or sulphur, which is optionally monosubstituted to polysubstituted by identical or different substituents, suitable substituents in each case being: halogen, cyano, in each case straight-chain or branched alkyl, alkoxy, halogenoalkyl, halogenoalkoxy, alkylcarbonyl or alkoxycarbonyl, each having 1 to 6 carbon atoms in the individual alkyl moieties and in the case of the halogenoalkyl or halogenoalkoxy radical, each having 1 to 9 identical or different halogen atoms; furthermore for straight-chain or branched dialkylaminoalkyl, each having 1 to 6 carbon atoms in the individual alkyl moieties, furthermore for cycloalkyl having 1 to 6 carbon atoms in the straight-chain or branched alkyl moiety and 3 to 7 carbon atoms in the cycloalkyl moiety, which is optionally monosubstituted to polysubstituted in the cycloalkyl moiety by identical or different substituents from the series comprising halogen and/or straight-chain or branched alkyl having 1 to 4 carbon atoms, or for phenylethyl which is optionally monosubstituted to polysubstituted in the phenyl moiety by identical or different substituents from the series comprising cyano, halogen and/or in each case straight-chain or branched alkyl or alkoxy, each having 1 to 4 carbon atoms, $R^3$ stands for hydrogen or for straight-chain or branched alkyl having 1 to 6 carbon atoms, and $R^4$ stands for cyano or for in each case straight-or branched alkanoyl, alkoxycarbonyl, alkylaminocarbonyl, dialkylaminocarbonyl, alkylsulphinyl or alkylsulphonyl, each having 1 to 6 carbon atoms in the individual alkyl moieties, or for phenylsulphinyl or phenylsulphonyl.

Particularly preferred compounds of the formula (I) are those in which

R stands for a

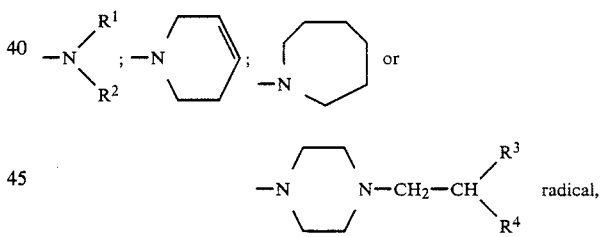

where $R^1$ stands for in each case substituted methyl, ethyl or n- or i-propyl and also n-, i- or s-butyl, suitable substituents in each case being: cyano, methoxy, ethoxy, methylcarbonyl, ethylcarbonyl, methoxycarbonyl, ethoxycarbonyl, methylaminocarbonyl, dimethylaminocarbonyl, ethylaminocarbonyl, diethylaminocarbonyl, methylsulphinyl, methylsulphonyl, dimethylamino, diethylamino or dipropylamino, dibutylamino or cyclohexyl; furthermore for allyl, n- or i-butenyl, propargyl, n- or i-butinyl, for cyclopentyl, cyclohexyl and cyclopropyl or for benzyl or phenyl, each of which is optionally monosubstituted, disubstituted or trisubstituted in the phenyl moiety by identical or different substituents, suitable substituents being: fluorine, chlorine, bromine, cyano, methyl, ethyl, n- or i-propyl, n-, i- or s-butyl, methoxy, ethoxy, trifluoromethyl, trifluoromethoxy, acetyl, methoxycarbonyl or ethoxycarbonyl, $R^2$ stands for heterocyclylmethyl, heterocyclylethyl or heterocyclylpropyl, each of which is optionally monosubstituted or disubstituted in the heterocyclyl moiety by identical or different substituents, suitable heterocyclyl radicals in each case being one of the following radicals.

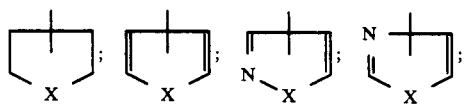

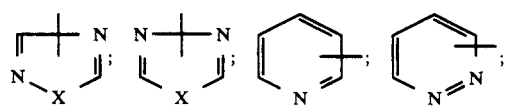

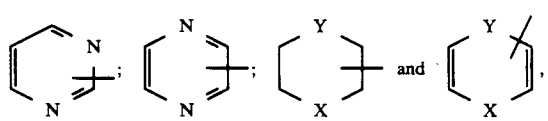

where

X in each case stands for oxygen, sulphur or an NH group and Y in each case stands for oxygen, sulphur, an NH group or a $CH_2$ group, suitable substituents in each case being: fluorine, chlorine, bromine, cyano, methyl, ethyl, n- or i-propyl, n-, i-, s- or t-butyl, methoxy, ethoxy, trifluoromethyl, trifluoromethoxy, acetyl, methoxycarbonyl or ethoxycarbonyl; furthermore for dimethylaminoethyl, diethylaminoethyl, dimethylaminopropyl, diethylaminopropyl, dipropylaminopropyl, dibutylaminopropyl, dibutylaminobutyl, dibutylaminoethyl, dipropylaminoethyl, dimethylaminobutyl, diethylaminobutyl, dimethylaminopentyl and diethylaminopentyl, for cyclohexylmethyl or cyclohexylethyl which are in each case optionally monosubstituted, disubstituted or trisubstituted by identical or different substituents from the series comprising methyl, ethyl and/or isopropyl, or for phenethyl which is optionally monosubstituted, disubstituted or trisubstituted by identical or different substituents from the series comprising fluorine, chlorine, bromine, cyano, methyl, ethyl, n- or i-propyl, n-, i-, s- or t-butyl, methoxy, ethoxy, n- or i-propoxy and n-, i-, s- or t-butoxy, R3 stands for hydrogen, methyl, ethyl, n- or i-propyl and also n-, i-, s- or t-butyl, and $R^4$ stands for cyano, acetyl, propionyl, methoxycarbonyl, ethoxycarbonyl, methylaminocarbonyl, dimethylaminocarbonyl, ethylaminocarbonyl, diethylaminocarbonyl, dipropylaminocarbonyl, dibutylaminocarbonyl, methylsulphinyl, ethylsulphinyl, methylsulphonyl, ethylsulphonyl, phenylsulphinyl or phenylsulphonyl. Very particularly preferred compounds of the formula (I) are those in which R stands for a

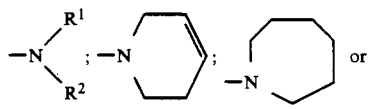

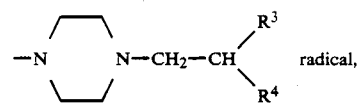

where $R^1$ stands for methyl, ethyl, n- or i-propyl, n-, i- or s-butyl, allyl, propargyl, for cyclohexyl, cyclopropyl, cyclopentyl, cyclohexylmethyl, phenyl, benzyl or for cyanoethyl, $R^2$ stands for heterocyclylmethyl, heterocyclylethyl or heterocyclylpropyl, each of which is optionally monosubstituted, disubstituted or trisubstituted by identical or different substituents from the series comprising chlorine and methyl, suitable heterocyclyl radicals being:

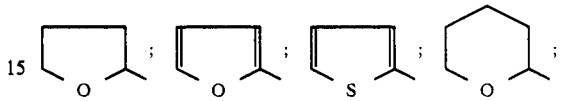

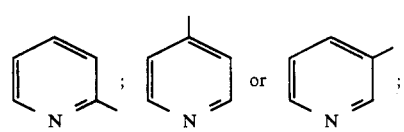

or for 2-heterocyclylethyl, 2-heterocyclylpropyl or 3-heterocyclylpropyl, each of which is monosubstituted, disubstituted or trisubstituted by identical or different substituents from the series comprising methyl and ethyl, suitable heterocyclyl radicals being:

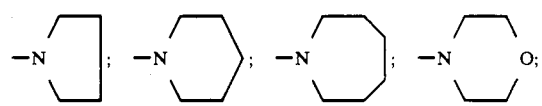

furthermore for diethylaminoethyl, dimethylaminopropyl, diethylaminopropyl, dibutylaminopropyl or diethylaminopentyl, for cyclohexylmethyl or for phenethyl, $R^3$ stands for hydrogen and $R^4$ stands for cyano, acetyl, propionyl, methoxycarbonyl, ethoxycarbonyl, dimethylaminocarbonyl, for methylsulphinyl, methylsulphonyl, phenylsulphinyl or phenylsulphonyl.

Especially preferred compounds of the formula (I) are those in which R stands for

is radical, where $R^1$ stands for cyanoethyl and $R^2$ stands for heterocyclylmethyl, heterocyclylethyl or heterocyclylpropyl, each of which is optionally monosubstituted, disubstituted or trisubstituted by identical or different substituents from the series comprising chlorine and methyl, suitable heterocyclyl radicals being:

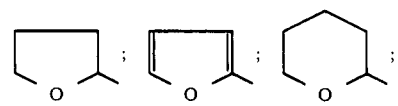

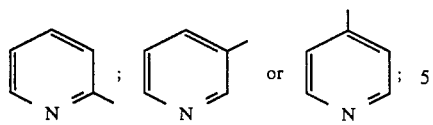

or for 2-heterocyclylethyl, 2-heterocyclylpropyl or 3-heterocyclylpropyl, each of which is optionally monosubstituted, disubstituted or trisubstituted by identical or different substituents from the series comprising methyl and ethyl, suitable heterocyclyl radicals being:

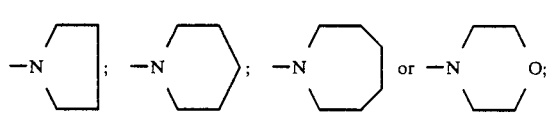

furthermore for diethylaminoethyl, dimethylaminopropyl, diethylaminopropyl, dibutylaminopropyl or diethylaminopentyl, for cyclohexylmethyl or phenethyl.

Besides these, especially preferred compounds of the formula (I) are also those in which R stands for a

radical,
where $R^1$ stands for methyl, ethyl, n- or i-propyl, n-, i- or s-butyl, allyl, propargyl, for cyclopropyl, cyclopentyl, cyclohexyl, cyclohexylmethyl, phenyl, benzyl or cyanoethyl, and $R^2$ stands for heterocyclylmethyl which is optionally monosubstituted, disubstituted or trisubstituted by identical or different substituents from the series comprising chlorine and methyl, suitable heterocyclyl radicals being:

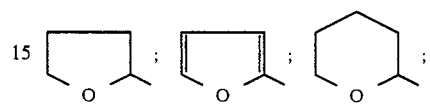

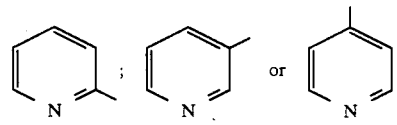

In addition to the compounds mentioned in the Preparation Examples, the following 1-aminomethyl-3-(2-fluoro-3-chlorophenyl)-4-cyano-pyrrole derivatives of the general formula (I) may be mentioned individually:

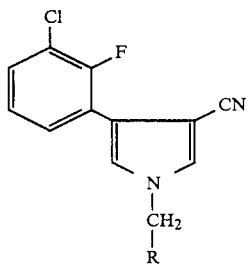

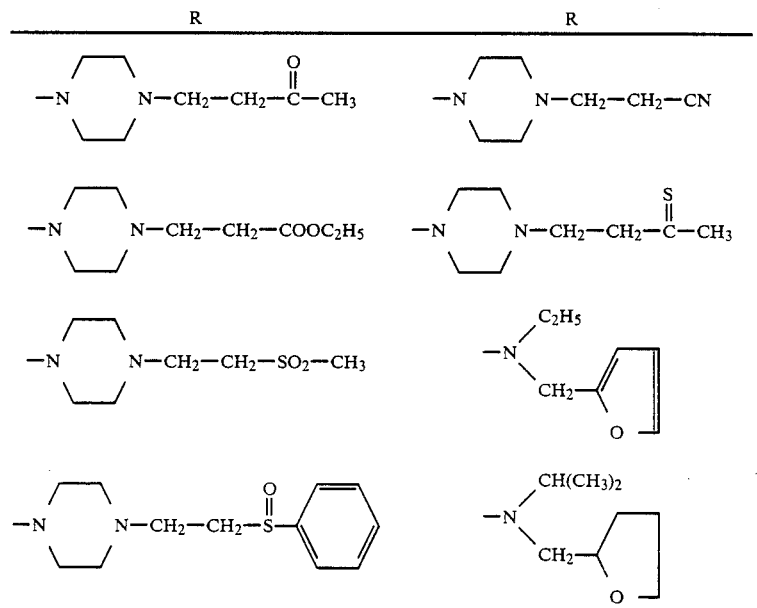

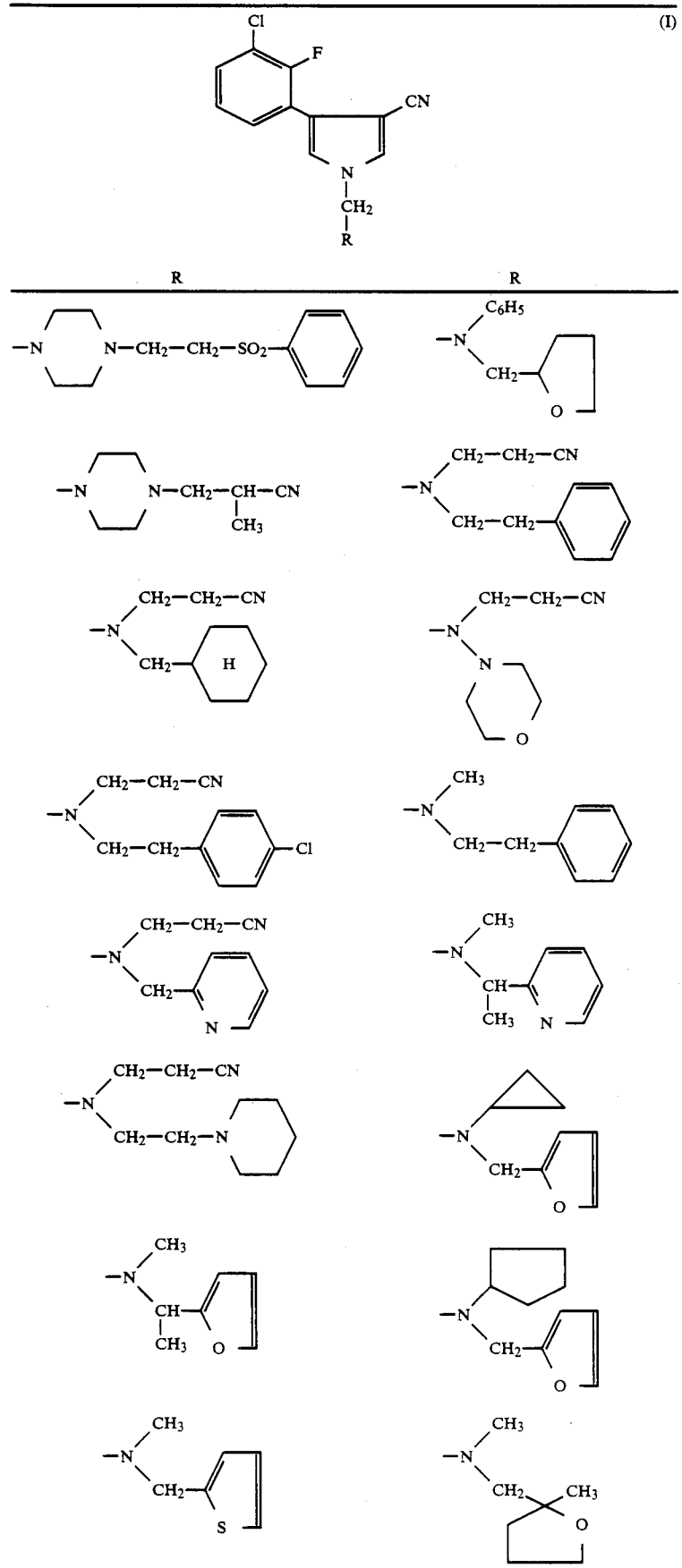

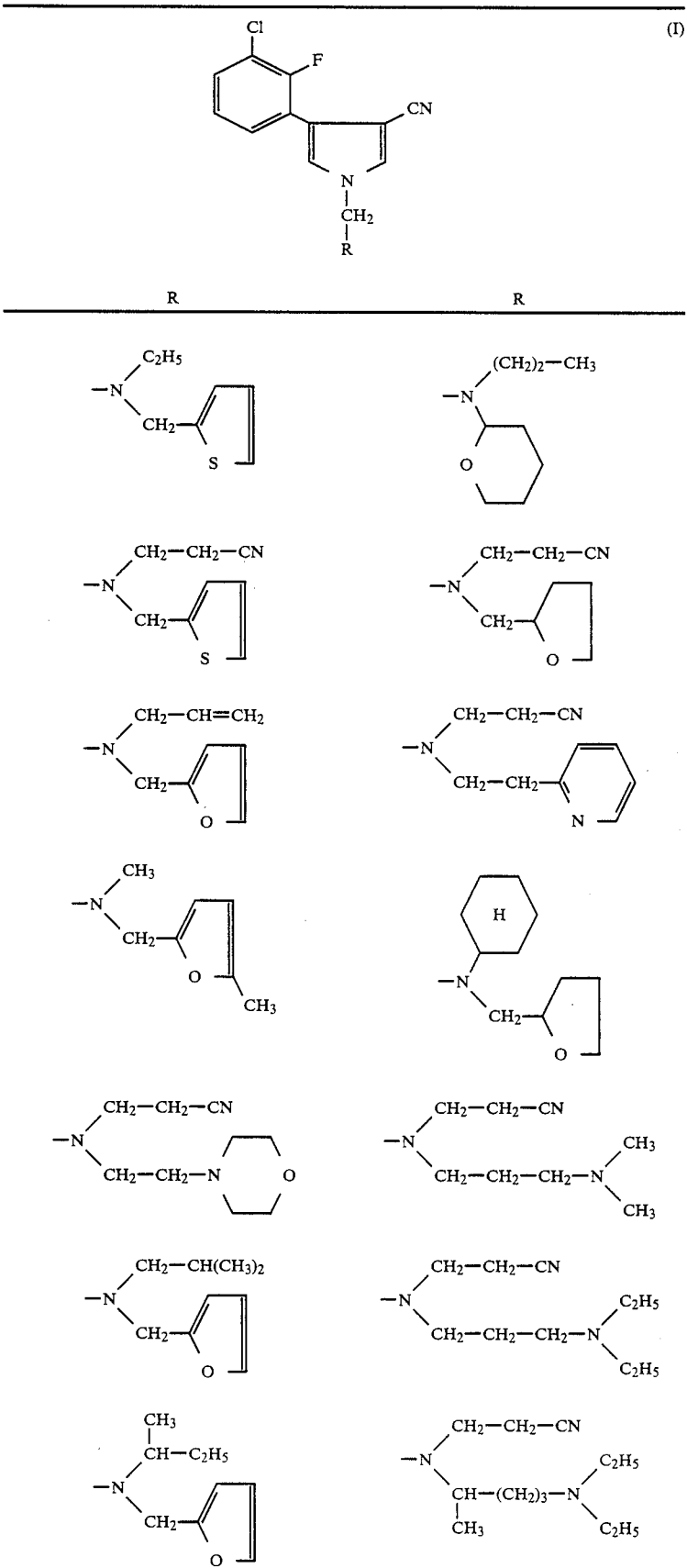

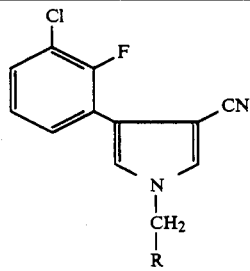
(I)
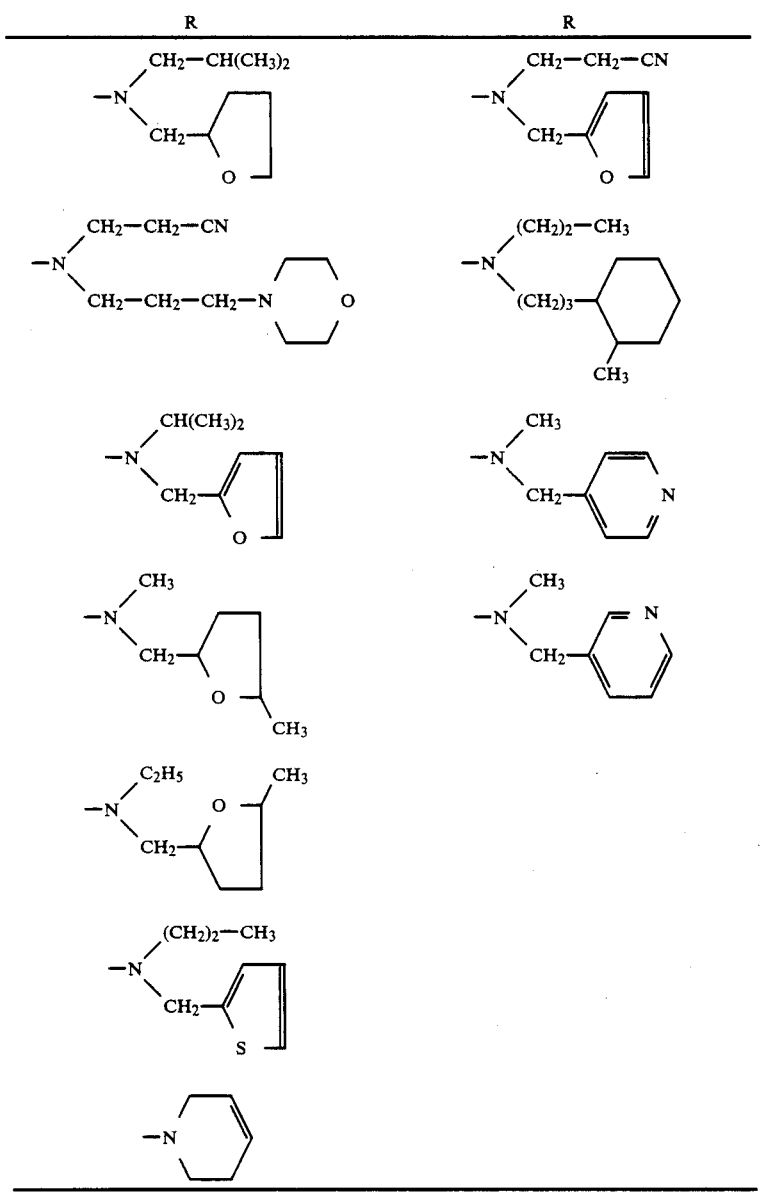
If, for example, 4-cyano-3-(2-fluoro-3-chlorophenyl)-pyrrole, formaldehyde and perhydroazepine are used as starting substances, the course of the reaction of process (a) according to the invention can be represented by the following equation:
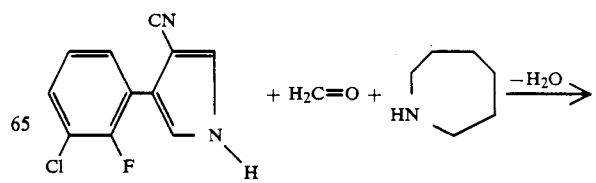

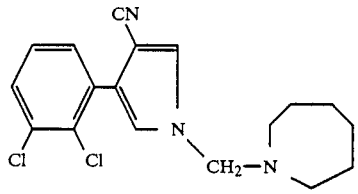

If, for example, 1-chloromethyl-4-cyano-3-(2-fluoro-3-chlorophenyl)-pyrrole and tetrahydropyridine are used as starting compounds, the course of the reaction of process (b) according to the invention may be represented by the following equation:

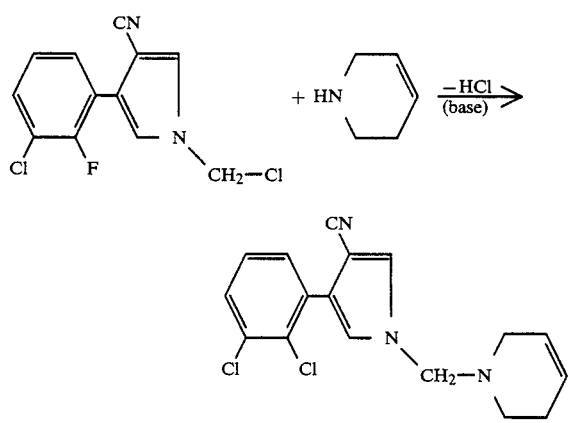

Formula (II) provides a definition of 3-(2-fluoro-3-chlorophenyl)-4-cyano-pyrrole which is required as starting compound for carrying out process (a) according to the invention.

3-(2-Fluoro-3-chlorophenyl)-4-cyano-pyrrole of the formula (II) is the subject matter of German Patent Application No. P 3,737,984, filed November 9, 1987, corresponding to U.S. Pat. No. 4,960,789 and can be obtained by the processes described therein, for example, when the known 2-fluoro-3-chloro-benzaldehyde of the formula (V)

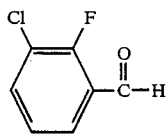

is subjected to a condensation reaction with cyanoacetic acid of the formula (VI)

NC—CH₂COOH     (VI)

in the customary manner in the presence of a base, such as, for example, piperidine or pyridine, and if appropriate in the presence of a suitable diluent, such as, for example pyridine, at temperatures between 50° C. and 120° C., with simultaneous decarboxylation (cf., for example, "Organikum" [Laboratory Practice of Organic Chemistry]pp 571/752; 15th edition; VEB Deutscher Verlag der Wissenschaften Berlin 1981, and also the Preparation Examples), and the resulting cinnamonitrile of the formula (VII)

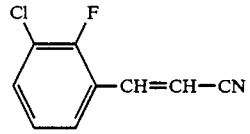

is reacted with p-toluenesulphonylmethyl isocyanide of the formula (VIII)

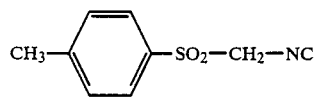

in the presence of a base, such as, for example, sodium hydride and if appropriate in the presence of a diluent, such as, for example, tetrahydrofuran, at temperatures between −20° C. and +50° C. (cf. also the Preparation Examples).

2-Fluoro-3-chlorobenzaldehyde of the formula (V) is known (cf., for example, DE-OS (German Published Specification) No. 3,129,274 or EP No. 61,907).

p-Toluenesulphonylmethyl isocyanide of the formula (VIII) is also known (cf., for example, Synthesis 1985, 400–402; Tetrahedron Lett. 1972, 2367–2368).

Formula (IV) provides a general definition of the 3-(2-fluoro-3-chlorophenyl)-4-cyano-pyrroles required as starting substances for carrying out process (b) according to the invention. In this formula (IV), E preferably stands for hydroxyl or halogen, especially for chlorine.

The 3-(2-fluoro-3-chlorophenyl)-4-cyano-pyrroles of the formula (IV) have not been known hitherto. However, they are obtained by known processes (cf. EP 133,247) when 3-(2-fluoro-3-chlorophenyl)-4-cyano-pyrrole of the formula (II)

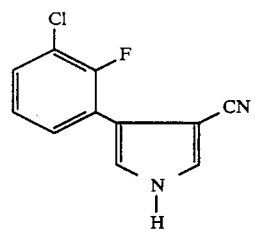

is reacted with formaldehyde at temperatures between 20° C. and 160° C., if appropriate in the presence of a customary diluent, such as, for example, tetrahydrofuran and if appropriate in the presence of a halogenating agent such as, for example, thionyl chloride or phosphorus oxychloride, and if appropriate in the presence of an acid-binding agent such as, for example, triethylamine or diazabicycloundecene (DBU).

Formula (III) provides a general definition of the amines also required as starting substances for carrying out processes (a) and (b) according to the invention. In this formula (III), R preferably stands for those radicals which have already been mentioned in connection with the description of the substances of the formula (I) according to the invention as being preferred for this substituent.

The amines of the formula (III) are generally known compounds of organic chemistry or can be obtained in analogy to known processes (cf., for example, GB 1,031,916 dated 2.6.1966; Org. Magnet. Res. 7, 488–495 [1975]; Kogyo Kagaku Zasshi 63, 1593–1597 [1960] or CA 60: 10 542 f).

Suitable diluents for carrying out process (a) according to the invention are inert organic solvents or aqueous systems. Protic solvents, for example alcohols, such as methanol, ethanol or propanol, or carboxylic acids, such as formic acid, acetic acid or propionic acid, or mixtures thereof with water, are preferably used. It is also possible for process (a) according to the invention to be carried out in aprotic solvents. These include in particular aliphatic or aromatic optionally halogenated hydrocarbons, such as, for example, benzine, benzene, toluene, xylene, chlorobenzene, petroleum ether, hexane, cyclohexane, dichloromethane, chloroform, carbon tetrachloride or ethers, such as diethyl ether, dioxane, tetrahydrofuran or ethylene glycol dimethyl or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate or sulphoxides, such as dimethyl sulphoxide.

If appropriate, process (a) according to the invention is carried out in the presence of a suitable reaction auxiliary. Suitable for this purpose are either catalytic to equimolar amounts of an organic or inorganic acid or appropriate amounts of a suitable base. Suitable acid reaction auxiliaries are in particular inorganic mineral acids, such as phosphoric acid, sulphuric acid, nitric acid, hydrochloric acid or hydrobromic acid, or organic acids, such as formic acid, acetic acid, propionic acid, methanesulphonic acid, benzenesulphonic acid or toluenesulphonic acid.

Suitable basic reaction auxiliaries are all customary inorganic or organic bases. These include for example alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

However, it is also possible to use a suitable excess of the amine of the formula (III), which is used as a reactant, simultaneously as a reaction auxiliary.

When carrying out process (a) according to the invention, the reaction temperatures can be varied within a relatively wide range. In general, the process is carried out at temperatures between 0° C. and 120° C., preferably at temperatures between 20° C. and 90° C.

For carrying out process (a) according to the invention, 1.0 to 2.0 moles, preferably 1.0 to 1.5 moles, of amine of the formula (III) and 1.0 to 2.0 moles, preferably 1.0 to 1.5 moles, of formaldehyde are generally employed per mole of 3-aryl-4-cyano-pyrrole of the formula (II). The formaldehyde is employed either in the form of an aqueous solution, as paraformaldehyde or as 1,3,5-trioxane. An aqueous solution is preferably used.

The reaction is carried out, and the reaction products of the formula (I) are worked up and isolated in analogy to known processes (cf. EP No. 133,247).

Suitable diluents for carrying out process (b) according to the invention are inert organic solvents. These include in particular aliphatic or aromatic optionally halogenated hydrocarbons, such as, for example, benzine, benzene, toluene, xylene, chlorobenzene, petroleum ether, hexane, cyclohexane, dichloromethane, chloroform, carbon tetrachloride and ethers, such as diethyl ether, dioxane, tetrahydrofuran or ethylene glycol dimethyl or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

If appropriate, process (b) according to the invention is carried out in the presence of a suitable acid-binding agent. Suitable acid-binding agents are all customary inorganic or organic bases. These include for example alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

However, it is also possible to employ an appropriate excess of the amine of the formula (III), which is a suitable reactant, simultaneously as a reaction auxiliary.

When carrying out process (b) according to the invention, the reaction temperatures can be varied within a relatively wide range. In general, the process is carried out at temperatures between 0° C. and 100° C., preferably at temperatures between 20° C. and 60° C.

For carrying out process (b) according to the invention, 1.0 to 2.0 moles, preferably 1.0 to 1.5 moles, of amine of the formula (III) and if appropriate 1.0 to 2.0 moles, preferably 1.0 to 1.5 moles, of acid-binding agent are generally employed per mole of 3-aryl-4-cyanopyrrole of the formula (IV). The reaction is carried out, and the reaction products of the formula (I) are worked up and isolated in analogy to known processes.

The active compounds according to the invention exhibit a powerful action against pests and can be employed in practice for combating of undesired noxious organisms. The active compounds are suitable for example for the use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium);

Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides;* Sclerotinia species, such as for example, *Sclerotinia Sclerotiorum..*

The good toleration, by plants, of the active compounds, at the concentrations required for combating plant diseases, permits treatment of above-ground parts of plants, of vegetative propagation stock and seeds, and of the soil.

Here, the active compounds according to the invention can be employed with particularly good success for combating rice diseases, such as, for example, against the causative organism of rice blast disease (*Pyricularia oryzae*) or for combating diseases in fruit and vegetable growing, such as, for example, against the causative organism of gray mold (*Botrytis cinerea*). Furthermore, the good in vitro activity of the compounds must be emphasized.

Depending on their respective physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold-mist and and warm-mist formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foam-ing, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

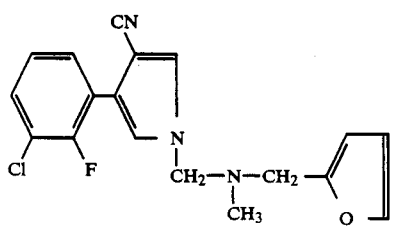

(Process a)

0.43 g (0.0057 mole) of 37 per cent aqueous formaldehyde solution and 0.05 ml of acetic acid are added to 1.2 g (0.00545 mole) of 4-cyano-3-(2-fluoro-3-chlorophenyl)-pyrrole in 10 ml of ethanol. 0.63 g (0.0057 mole) of N-methylfurfurylamine are then added dropwise and with stirring, and, when the addition is complete, the reaction mixture is stirred at room temperature for 20 hours. For working up, 50 ml of ethyl acetate are added, the mixture is washed three times using water and dried over sodium sulphate, the solvent is removed in vacuo and the residue is crystallized from ether/cyclohexane.

1.2 g (64% of theory) of 4-cyano-3-(2-fluoro-3-chlorophenyl)- chlorophenyl 1-(N-methyl-N-furfurylaminomethyl)-pyrrole of melting point 63°-64° C. are obtained.

PREPARATION OF THE STARTING COMPOUNDS

COMPOUND II

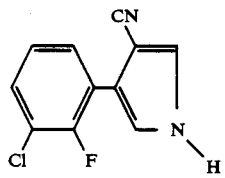

A solution of 6.0 g (0.0331 mole) of 3-(2-fluoro-3-chlorophenyl)-acrylonitrile and 7.8 g (0.0431 mole) of p-toluenesulphonylmethyl isocyanide in 20 ml of a mixture of tetrahydrofuran/dimethyl sulphoxide (5:1) is added dropwise, with stirring, at −10° C. to −20° C. and under an argon protective gas atmosphere to 1.4 g (0.0464 mole) of sodium hydride (80% strength in mineral oil) in 17.5 ml of tetrahydrofuran. When the addition is complete, the reaction mixture is allowed to warm to room temperature, water is added, the mixture is extracted several times using ethyl acetate, and the combined ethyl acetate phases are washed with water, dried over sodium sulphate and evaporated in vacuo. The residue is purified by chromatography on silica gel (eluent: cyclohexane/ethyl acetate 5:1).

3.3 g (45% of theory) of 3-cyano-4-(2-fluoro-3-chlorophenyl)-pyrrole of melting point 180°-181° C. are obtained.

COMPOUND VII

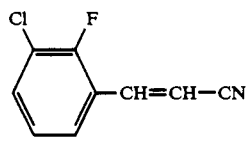

2.5 ml of piperidine and 22.9 g (0.27 mole) of cyanoacetic acid are added to a solution of 40.1 g (0.25 mole) of 2-fluoro-3-chlorobenzaldehyde in 170 ml of pyridine, and the mixture is refluxed for 14 hours. For working up, the mixture is evaporated in vacuo, the residue is taken up in ethyl acetate, and the mixture is washed in succession with 1-normal hydrochloric acid, with aqueous sodium hydrogen sulphite solution and also with water, dried over sodium sulphate and concentrated in vacuo. The oil remaining can be purified by chromatography on silica gel (eluent: cyclohexane/ethyl acetate 5:1).

16.9 g (37% of theory) of 3-(2-fluoro-3-chlorophenyl)-acrylonitrile of melting point 90°-92° C. are obtained.

The following 1-aminomethyl-3-(2-fluoro-3-chlorophenyl)-4-cyano-pyrrole derivatives of the general formula (I) are obtained in a corresponding manner and in accordance with the general instructions for the preparation:

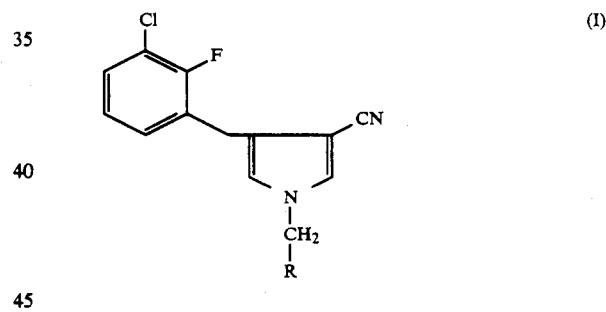

| Example No. | R | physical properties |
|---|---|---|
| 2 | —N(C₂H₅)(CH₂-furyl) | ¹H-NMR*: 4.8–5.1 |
| 3 | —N(CH₃)(CH₂-furyl) | ¹H-NMR*: 4.7–5.0 |
| 4 | —N(CH₂—CH₂—CN)(CH₂—CH₂—N(C₂H₅)₂) | ¹H-NMR*: 4.9 |

-continued

| Example No. | R | physical properties |
|---|---|---|
| 5 | -N(CH₂-CH₃)(CH₂-furan) with (CH₂)—CH₃ | ¹H-NMR*: 4.8–5.1 |
| 6 | -N(CH₂-cyclohexyl-H)(CH₂-furan) | m.p. 87–88° C. |
| 7 | -N((CH₂)₂—CH₃)(CH₂-furan) | ¹H-NMR*: 4.7–5.1 |
| 8 | -N(azepane) | ¹H-NMR*: 4.8 |
| 9 | -N(cyclohexyl-H)(CH₂-furan) | ¹H-NMR*: 4.8 |
| 10 | -N(CH₃)(CH₂—CH₂-pyridyl) | m.p. 74–75° C. |
| | -N(CH₃)(CH₂-pyridyl) | ¹H-NMR*: 4.8 |
| | -N(C₂H₅)(CH₂—CH₂—N(CH₃)(CH₃)) | ¹H-NMR*: 4.8 |

*The ¹H-NMR spectra were recorded in CDCl₃ with tetramethylsilane (TMS) as the internal standard.
The chemical shift of the protons

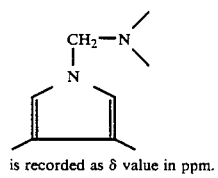

is recorded as δ value in ppm.

EXAMPLE A

Botrytis test (bean)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humid chamber at 20° C. 3 days after the inoculation, the size of the infected spots on the leaves is evaluated.

In this test, for example, the compound of preparation Examples 1, 2, 3, 5, 6, 7 and 10 show a degree of effectiveness of 86% to 98% at 50 ppm.

EXAMPLE B

*Cochliobolus sativus* test (barley)/protective
Solvent: 100 parts dimethylformamide
Emulsifier: 0.25 parts alkylarylpolyglycolether To produce a suitable preparation of active compound 1 part by weight of active compound is mixed with the stated amounts of solvent and emulsifier and the concentrate is diluted with water to the desired concentration.

To test for protective activity young plants are sprayed with the preparation of active compound until dew-moist. After the spray-coating has dried on the plants are sprayed with a conodium suspension of *Cochliobolus sativus*. The plants are kept in an incubation chamber for 48 hours at 20° C. and at a relative atmosphere humidity of 100%.

The plants are placed in a greenhouse at a temperature of about 20° C. and at a relative atmospheric humidity of about 80%.

Evaluation is carried out 7 days after the inoculation.

In this test a distinctly superior activity compared with the prior art is shown, for example, by the compounds according to the preparation Examples 3, 5, 7, 9, 11 and 12.

EXAMPLE C

*Pyrenophora teres* test (barley)/protective
Solvent: 100 parts by weight dimethylformamide
Emulsifier: 0.25 parts by weight alkylarylpolyglycolether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried off, the plants are sprayed with a conidia suspension of *Pyrenophora teres*. The plants then remain in an incubation cabin at 20° C. and 100% relative atmospheric humidity for 48 hours.

The plants are placed in a greenhouse at a temperature of about 20° C. and a relative atmospheric humidity of about 80°.

Evaluation is carried out 7 days after the inoculation.

In this test, a clearly superior activity compared with the prior art is shown, for example, by the compounds according to the preparation Examples 3, 5, 6, 7, 9, 11 and 12.

EXAMPLE D

*Leptosphaeria nodorum*-test (wheat)/protective

Solvent: 100 parts by weight dimethylformamide
Emulsifier: 0.25 parts by weight alkylarylpolyglycolether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain in an incubation cabin at 20° C. and 100% relative atmospheric humidity for 48 hours.

The plants are placed in a greenhouse at a temperature of about 15° C. and a relative atmospheric humidity of about 80%.

Evaluation is carried out 10 days after the inoculation.

In this test, a clearly superior activity compared with the prior art is shown, for example, by the compounds according to the preparation Examples 2, 7 and 10.

It is understood that the specification and examples are illustrative but not limitative of the present invention and that other embodiments within the spirit and scope of the invention will suggest themselves to those skilled in the art.

We claim:

1. A 1-aminomethyl-3-(2-fluoro-3-chlorophenyl)-4-cyano-pyrrole derivative of the formula

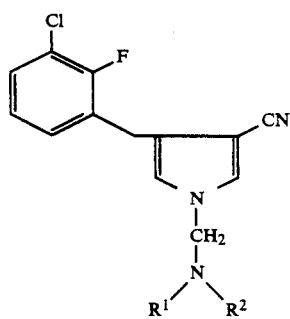

(I)

$R^1$ stand for methyl, ethyl, n- or i-propyl, n-, i-, or s-butyl, allyl, propargyl, cyclohexyl, cyclopropyl, cyclopentyl, cyclohexylmethyl, phenyl, benzyl, or cyanoethyl, $R^2$ stands for heterocyclylmethyl, heterocyclylethyl, or heterocyclylpropyl, each of which is optionally monosubstituted, disubstituted, or trisubstituted by identical or different substituents from the group consisting of chlorine and methyl, the heterocyclyl radicals being selected from the group consisting of:

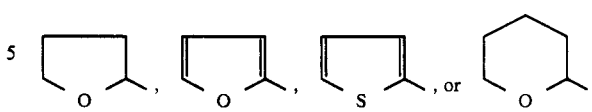

2. A 1-aminomethyl-3-(2-fluoro-3-chlorophenyl)-4-cyano-pyrrole derivative according to claim 1, in which $R^1$ stands for cyanoethyl.

3. A compound according to claim 1, wherein such compound is 4-cyano-3-(2-fluoro-3-chlorophenyl)-1-(N-ethyl-N-tetrahydrofurfuryl-aminomethyl)-pyrrole of the formula

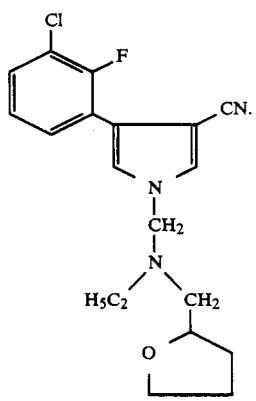

4. A compound according to claim 1, wherein such compound is 4-cyano-3-(2-fluoro-3-chlorophenyl)-1-(N-methyl-N-tetrahydrofurfuryl-aminomethyl)-pyrrole of the formula

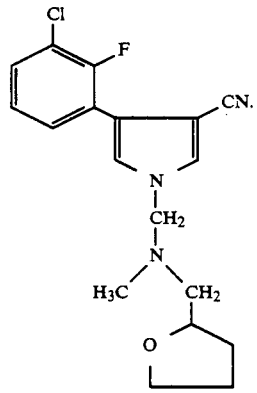

5. A compound according to claim 1, wherein such compound is 4-cyano-3-(2-fluoro-3-chlorophenyl)-1-(N-n-propyl-N—furfuryl-aminomethyl)-pyrrole of the formula 6. A compound according to claim 1, wherein such compound is 4-cyano-3-(2-fluoro-3-chlorophenyl)-1-(N-cyclohexyl-N—furfuryl-aminomethyl)-pyrrole of the formula

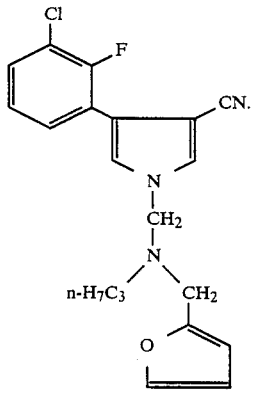

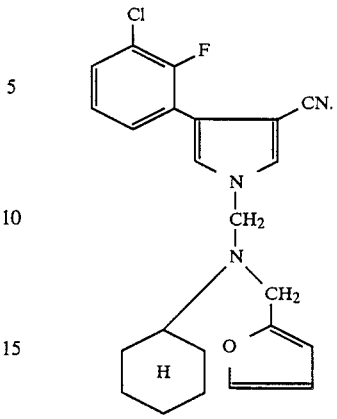

7. A fungicidal composition comprising a fungicidally effective amount of a compound according to claim 1 and a diluent.

8. A method of combating fungi which comprises applying to such fungi or to a fungus habitat a fungicidally effective amount of a compound according to claim 1.

9. The method according to claim 8, wherein such compound is
4-cyano-3-(2-fluoro-3-chlorophenyl)-1-(N-ethyl-N-tetrahydrofurfuryl-aminomethyl)-pyrrole,
4-cyano-3-(2-fluoro-3-chlorophenyl)-1-(N-methyl-N-tetrahydrofurfuryl-aminomethyl)-pyrrole,
4-cyano-3-(2-fluoro-3-chlorophenyl)-1-(N-n-propyl-N—furfuryl-aminomethyl)-pyrrole, or
4-cyano-3-(2-fluoro-3-chlorophenyl)-1-(N-cyclohexyl-N—furfuryl-aminomethyl)-pyrrole.

* * * * *